US00PP07864P

United States Patent [19]

Lopez

[11] Patent Number: Plant 7,864

[45] Date of Patent: May 12, 1992

[54] STRAWBERRY PLANT NAMED MILSEI

[75] Inventor: Jose M. A. Lopez, Tudela Navarra, Spain

[73] Assignee: Plantas de Navarra S.A., Navarra, Spain

[21] Appl. No.: 564,446

[22] Filed: Aug. 8, 1990

[51] Int. Cl.[5] ..... A01H 5/00
[52] U.S. Cl. ..... Plt./48
[58] Field of Search ..... Plt. 48, 49

[56] References Cited

U.S. PATENT DOCUMENTS

P.P. 1,848 6/1959 Hartman ..... Plt. 48

*Primary Examiner*—Howard J. Locker
*Attorney, Agent, or Firm*—Foley & Lardner

[57] ABSTRACT

A strawberry plant named Milsei particularly characterized by its generally round leaves, large white flowers, generally cylindrical fruit wherein the exterior surface is smooth, glossy and red, and the flesh and core orange-red; calyx diameter similar to the diameter of the fruit; achenes recessed below the surface, vigorous growth habit, firm exterior, flesh and core, and its medium to strong juiciness and flavor.

2 Drawing Sheets

The present invention relates to a new and distinctive cultivar of strawberry plant referred to by the varietal name Milsei. The new cultivar was referred to by the number 85.116.10 during breeding and development. The new cultivar is a product of a planned breeding program. The basic objective of the breeding program was to create new strawberry cultivars particularly adaptable to growing conditions in Huelva, Spain with regard to fruit production, size, taste and color. The geographical location of Huelva, Spain is 7° West and 37° North, near the Gulf of Cadiz.

The new cultivar was originated from a cross made in a controlled breeding program in Valtierra, Navarra, Spain. The female parent was the cultivar named Parker, and the male parent was the cultivar named Chandler.

Milsei was discovered and selected by me as a plant within the progeny of the stated cross in a controlled environment in Huelva, Spain. Asexual reproduction of the new variety, as performed by me at Soria, Spain, has demonstrated that the combination of characteristics as herein disclosed for the new cultivar are firmly fixed and are retained through successive generations of asexual reproduction.

Milsei has not been observed under all possible environmental conditions. The phenotype may vary significantly with variations in environment. The following observations, measurements and values describe the new cultivar as grown in Huelva, Spain under conditions which closely approximate those generally used in commercial practice.

The following traits have been repeatedly observed and are determined to be basic characteristics of Milsei, which in combination distinguish this strawberry plant as a new and distinct variety:

1. The terminal leaflet is approximately as long as it is broad. Leaf color is medium to dark green, the pose of hairs of petiole is outward.

2. The fruit is much longer than its maximum width, and is very large.

3. Insertion of achenes is below the surface.

4. The diameter of the calyx is approximately the same as its fruit. In the male parent Chandler the calyx is longer.

5. The acidity of Milsei is relatively strong, more so than Chandler.

6. Plant vigor is strong; shape is flat to globose.

7. Flowers are large and generally level relative to foliage, with the peduncule semi-erect. Inflorescence is very abundant.

8. Fruit juiciness, sweetness and flavor are medium to strong. The firmness of the fruit is medium to strong.

9. Exterior fruit color is red, with the flesh and core being orange-red.

10. The shape of the exterior surface is relatively even and smooth, and the surface is very glossy.

The new cultivar is most similar to the male parent Chandler, being similar thereto in the characteristics enumerated in 6–10 above. Milsei distinguishes from Chandler by its more round leaves, more elongated and larger fruit, smaller diameter calyx, and its greater acidity.

The accompanying color photographic drawings show various features of typical specimen plants of the new cultivar.

Sheet 1 comprises a top photograph showing a number of plants with fruit in various stages of maturity, and a bottom photograph showing whole fruit and longitudinal and transverse sections through the fruit to show the flesh.

Sheet 2 comprises a top photograph showing the undersides of two leaves of different maturity and several flowers in bloom, and a bottom photograph showing the under surfaces of the calyx and the relationship between the diameter of the calyx and the flower. The colors appearing in the photographs are as true as possible with color illustrations of this type.

In the following description, color references are made to The Royal Horticultural Society Color Chart (R.H.S.), except where general colors of ordinary significance are referred to. Color values were taken at Huelva, Spain.

Parentage:

*Male parent.*—Parker.

*Female parent.*—Chandler.

Propagation: Medium to strong propagation; runners or stolons root easily and with strong vigor.

Plants:

A. *Shape.*—Flat, globose.

B. *Preferred planting.*—October in Huelva, Spain, with peak production occurring in March–May.

C. *Leaves.*—1. Size: Medium. 2. Shape: Terminal leaflet is as long as it is broad and base is obtuse; shape of teeth is obtuse. 3. Color: Top surface medium to dark green, mature color approximately 136 A-B; under surface near 148 B-C. 4. Growth Habit: Flat, globose. 5. Other Characteristics: Pose of hairs of petiole outwards.

Inflorescence:

A. *Size and shape.*—Flowers are large and positioned relatively level to foliage.

B. *Peduncles.*—Semi-erect.

C. *Pedicels.*—Normal, one flower per pedical; hairs upward.

D. *Quantity.*—Very abundant.

E. *Color.*—White.

F. *Anthers and pollen.*—Abundant and fertile.

G. *Calyx.*—Inner and outer calyx approximately the said size, as is the size of calyx in relation to fruit diameter.

Fruit:

A. *Overall size and shape.*—Size is very large; shape is generally cylindrical and much longer than broad.

B. *Achenes.*—Appear recessed below the surface.

C. *Juiciness.*—Medium to heavy.

D. *Taste.*—Sweetness and flavor is medium to strong, although acidic.

E. *Color.*—Red exterior, approximately 45A; flesh and core are orange-red, approximately 44A.

F. *Exterior surface.*—1. Gloss: very strong. 2. Texture: even. 3. Firmness: Medium to strong, similar to Chandler.

G. *Characteristics of flesh and core.*—Flesh is firm and same color as core.

H. *Aroma.*—Aromatic.

I. *Keeping qualities.*—Very good.

Disease resistance: No special sensitivities to disease or parasites have been observed to date.

I claim:

1. A new and distinct cultivar of strawberry plant named Milsei, as illustrated and described.

* * * * *

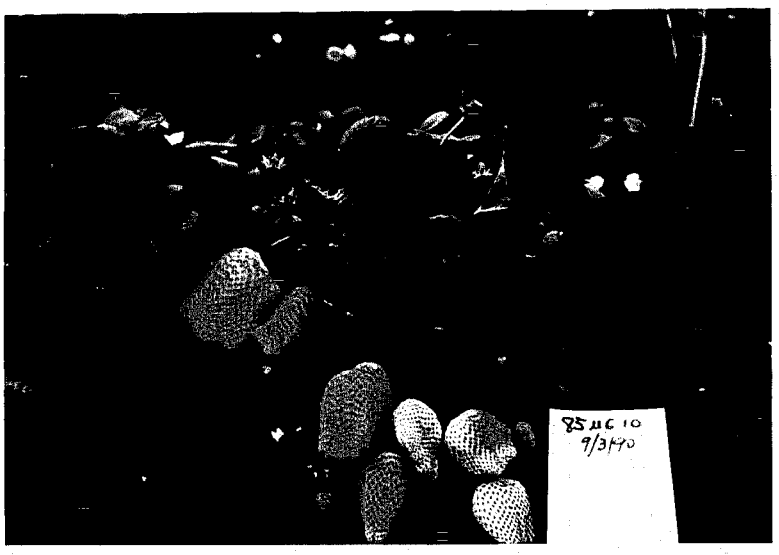
85 UC 10
9/3/90
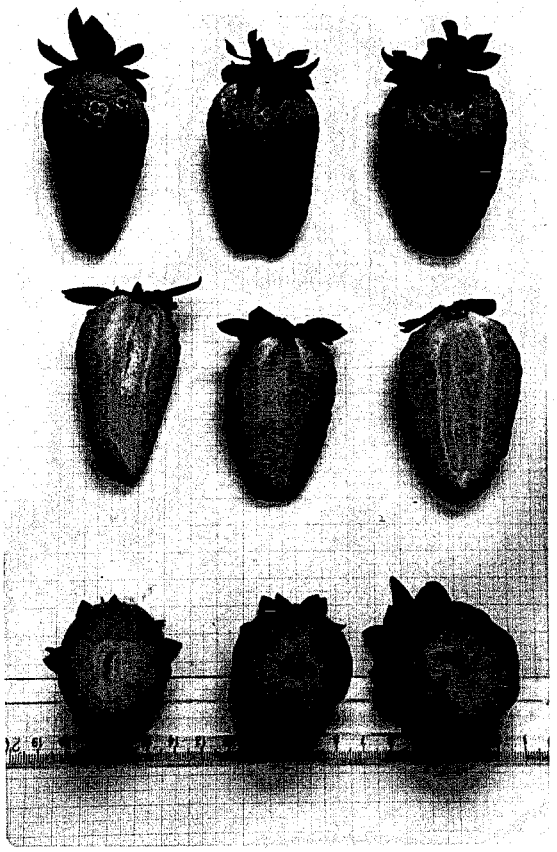

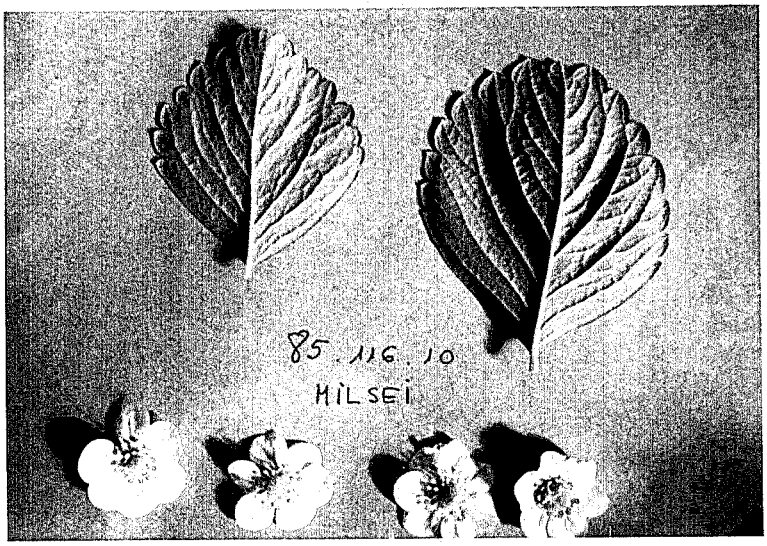
85.116.10
HILSEI
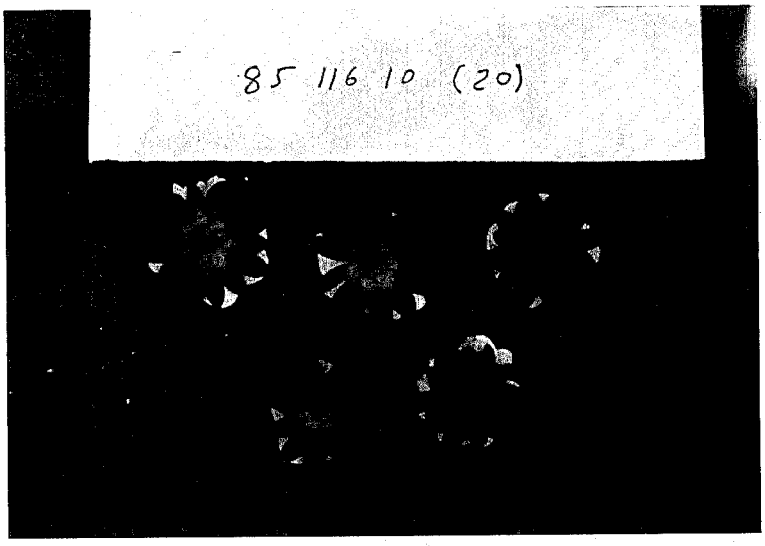
85 116 10 (20)